(12) United States Patent
Krishnan et al.

(10) Patent No.: US 7,653,227 B2
(45) Date of Patent: Jan. 26, 2010

(54) HIERARCHICAL MODELING IN MEDICAL ABNORMALITY DETECTION

(75) Inventors: Sriram Krishnan, Exton, PA (US); Jinbo Bi, Exton, PA (US); R. Bharat Rao, Berwyn, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 745 days.

(21) Appl. No.: 11/054,600

(22) Filed: Feb. 8, 2005

(65) Prior Publication Data

US 2005/0209519 A1    Sep. 22, 2005

Related U.S. Application Data

(63) Continuation-in-part of application No. 10/876,803, filed on Jun. 25, 2004.

(60) Provisional application No. 60/543,076, filed on Feb. 9, 2004.

(51) Int. Cl.
*G06K 9/00* (2006.01)
*A61B 6/00* (2006.01)

(52) U.S. Cl. .................. 382/128; 382/224; 378/21

(58) Field of Classification Search ............ 382/100, 382/128, 129, 130, 131, 133, 134, 156, 159, 382/168, 181, 190, 194, 199, 203, 209, 224, 382/232, 240, 260, 274, 276, 305, 103, 132; 600/300, 438; 702/181; 378/21
See application file for complete search history.

(56) References Cited

U.S. PATENT DOCUMENTS

| 5,195,525 | A |   | 3/1993 | Pelc |
|---|---|---|---|---|
| 5,769,074 | A | * | 6/1998 | Barnhill et al. ............ 600/300 |
| 5,803,914 | A |   | 9/1998 | Ryals et al. |
| 6,053,869 | A |   | 4/2000 | Kawagishi et al. |
| 6,099,469 | A |   | 8/2000 | Armstrong et al. |
| 6,247,004 | B1 |   | 6/2001 | Moukheibir |
| 6,248,063 | B1 |   | 6/2001 | Barnhill et al. |
| 6,352,507 | B1 |   | 3/2002 | Torp et al. |
| 6,537,221 | B2 |   | 3/2003 | Criton et al. |
| 6,674,879 | B1 |   | 1/2004 | Weisman et al. |

(Continued)

FOREIGN PATENT DOCUMENTS

WO         99/49775 A      10/1999

OTHER PUBLICATIONS

L Motet, Decision Trees and Diagrams, ACM Computing Surveys, New York, NY, US, vol. 14, No. 4, Dec. 1982, pp. 593-623.*

(Continued)

*Primary Examiner*—Seyed Azarian

(57) ABSTRACT

Hierarchal modeling is used to distinguish one state or class from three or more classes. In a first stage, a normal or other class is distinguished from a diseased or other groups of classes. If the results of the first stage classification indicate diseased or data within the groups of different classes, a subsequent stage of classification is performed. In a subsequent stage of classification, the data is classified to distinguish one or more other classes from the remaining classes. Using two or more stages, medical information is classified by eliminating one or more possible classes in each stage to finally identify a particular class most appropriate or probable for the data.

22 Claims, 2 Drawing Sheets

U.S. PATENT DOCUMENTS

| | | | | |
|---|---|---|---|---|
| 6,682,485 | B2* | 1/2004 | Seitz et al. | 600/438 |
| 6,801,916 | B2 | 10/2004 | Roberge et al. | |
| 7,043,063 | B1 | 5/2006 | Noble et al. | |
| 7,058,210 | B2* | 6/2006 | Mundy et al. | 382/128 |
| 7,123,762 | B2* | 10/2006 | Giger et al. | 382/132 |
| 2003/0120134 | A1* | 6/2003 | Rao et al. | 600/300 |
| 2003/0120458 | A1* | 6/2003 | Rao et al. | 702/181 |
| 2004/0176678 | A1 | 9/2004 | Murphy et al. | |
| 2004/0208341 | A1* | 10/2004 | Zhou et al. | 382/103 |
| 2005/0010098 | A1 | 1/2005 | Frigstad et al. | |

OTHER PUBLICATIONS

"Echocardiography (Echo) Section (Overview)," located on the Leiden University Medical website (http://www.lumc.nl/1010/LKEBHome/english/research/Echo/LKEBechoMain.html; printed on Feb. 4, 2005; 3 pgs.

"Echocardiography Section Stress Echo Analysis (BTS 00123) Title: Automated Quantitative Analysis of Echo Images of the Heart," located on the Leiden University Medical website (http://www.lumc.nl/1010/LKEBHome/english/research/Echo/Stress_BTS/LKEBechoProject.html; printed on Feb.4, 2005; 3 pgs; by J.G. Bosch and G. Van Burken; Sep. 2001.

"Echocardiography Section Stress Echo Analysis (STW LGN.4349) Title: Objective and Reproducible Quantitative Assessment of Left Ventricular Function from Stress Echocardiograms," located on the Leiden University Medical website (http://www.lumc.nl/1010/LKEBHome/english/research/Echo/Strees_STW/LKEBechoProject.html; printed on Feb. 4, 2005; 3 pgs.

"Echocardiography Section Analysis Station for Quantitative Echocardiography (STW LGN92.1706) Title: Development, Implementation and Evaluation of an Automated Station for Quantitative Echocardiography," located on the Leiden University Medical website (http://www.lumc.nl/1010/LKEBHome/english/research/Echo/EchoCMS/LKEBechoProject.html; printed on Feb. 4, 2005; 4 pgs.

"Knowledge Guided Image Processing (KGB) Section," located on the Leiden University Medical website (http://www.lumc.nl/1010/LKEBHome/english/research/KGB/LKEBKMain.html; printed on Feb. 4, 2005; 3 pgs.

Moret, "Decision Trees and Diagrams", ACM Computing Surveys, New York, NY, US, vol. 14, No. 4, Dec. 1982, pp. 593-623.

Pattipati et al., "Application of heuristic search and information theory to sequential fault diagnosis", Intelligent Control, 1988. Proceedings, IEEE International Symposium on Arlington, VA, USA Aug. 24-26, 1988, Washington, DC, USA, IEEE Comput. Soc. PR, US Aug. 24, 1988, pp. 291-296.

Schiller et al., "Recommendations for quantitation of the left ventricle by two-dimensional echocardiography", American Society of Echocardiography Committee on Standards, Subcommittee on Quantitative of Two-Dimensional Echocardiograms, Journal of the American Society of Echocardiography: Official Publication of the American Society of Echocardiography, Sep.-Oct. 1989, vol. 2, No. 5, Sep. 1989, pp. 358-367.

L'Abbate et al., "Integration of multimodal data of cardiac diseases in a dynamic three-dimensional heart model", Computers in Cardiology, 1999 Hannover, Germany, Sep. 26-29, 1999, Piscataway, NJ, USA, IEEE, US, Sep. 26, 1999, pp. 277-280.

International Search Report including Notification of Transmittal of the International Search Report, International Search Report and Written Opinion of the International Search Authority, PCT Appln No. PCT/US2005/004188; mailed Jun. 28, 2005.

Carranza et al., "Wavelet-neural Processing for Computer Aided Diagnosis", World Automation Congress, 2002, Proceedings of the 5th Biannual Jun. 9-13, 2002, Piscataway, NJ, IEEE, vol. 13, Jun. 9, 2002, pp. 215-220.

Tsai et al., "A Computer-Aided System for Discrimination of Dilated Cardiomyopathy Using Echocardiographic Images", IEICE Transactions on Fundamentals of Electronics, Communications and Computer Sciences, Institute of Electronics Information and Comm. Eng., Tokyo, JP, vol. E78-A, No. 12, Dec. 1, 1995, pp. 1649-1654.

* cited by examiner

HIERARCHICAL MODELING IN MEDICAL ABNORMALITY DETECTION

RELATED APPLICATIONS

The present patent document is a continuation-in-part of application Ser. No. 10/876,803, filed Jun. 25, 2004, and claims the benefit of the filing date under 35 U.S.C. §119(e) of Provisional U.S. Patent Application Ser. No. 60/543,076, filed Feb. 9, 2004, both of which are hereby incorporated by reference.

BACKGROUND

The present invention relates to detection of medical abnormalities. In particular, abnormalities are diagnosed through application of a model.

Medical information, such as images, is analyzed to automatically identify an abnormality. Various imaging systems are available, such as computed tomography, magnetic resonance, x-ray, nuclear medicine, ultrasound, positron emission tomography or other imaging. In addition to imaging information, other clinical information, such as age, medical history, symptoms, or other indicators of a likelihood of coronary artery disease, are gathered and used for the assessment.

Classifiers are applied to the obtained data to diagnose any abnormality. Different abnormalities may be distinguished by the classifiers. For binary classification, a classifier distinguishes between two classes, such as normal and abnormal. Where three or more different classes exist, one versus all the rest or one versus one classification is applied. By performing a plurality of different classifications, a class represented by the data is identified.

Cardiac wall motion is analyzed to detect abnormalities. For example, echocardiography (e.g., stress echo) includes segmented wall motion analysis. The left ventricle wall is divided into a plurality of segments (e.g., 16 or 17) according to a standard recommended by the American Society of Echocardiography (ASE). Various standardized ultrasound views are obtained to acquire image data information for each left ventricular segment. The views are standardized such that plurality of segments is roughly in line with a presumed distribution of three major coronary artery segments. The echocardiographer visually inspects the acquired image data to access global function and regional abnormalities. Based on the cardiographer's assessment, a wall motion score is assigned to each segment in accordance with the ASE scoring scheme. The absolute and relative systolic excursion and timing of excursion is assessed to provide a report of negative (non-pathological) or positive (pathological) findings. The scoring system ranks are normal, hypokinesia, akinesia, dyskinesia and aneurysm. Such wall motion diagnosis may require significant training and experience on the part of the echocardiographer.

BRIEF SUMMARY

By way of introduction, the preferred embodiments described below include methods and systems for modeling of medical abnormality detection or for detecting abnormalities. Hierarchal modeling is used to distinguish one state from three or more states. In a first stage, a normal or other state is distinguished from a diseased or other groups of states. If the results of the first stage classification indicate diseased or data within the group of different states, a subsequent stage of classification is performed. In a subsequent stage of classification, the data is classified to distinguish one or more other states from the remaining states. Using two or more stages, medical information is classified by eliminating one or more possible states in each stage to finally identify a particular class most appropriate or probable for the data.

In a first aspect, a method is provided for modeling medical abnormality detection. Medical data representing one of at least three possible ranked states is obtained. With a processor, the medical data is classified between a first state and a group including at least two other states. Medical data is also classified with the processor between the second and third states. The second classification may be avoided where as the first classification indicates existence in the first state. Alternatively, multiple stages of classifications are performed even with a highly probable classification for comparison of probabilities.

In a second aspect, a system is provided from modeling in medical abnormality detection. A memory is operable to store medical data representing at least one of three possible ranked states. A processor is operable to apply to the medical data a first classifier in a hierarchal model. The first classifier is operable to distinguish between first and second groups of states of the at least three possible ranked states. The processor is also operable to apply to the medical data a second classifier in the hierarchal model. The second classifier is operable to distinguish between third and fourth groups of states of the at least three possible states. The third and fourth groups are sub-sets of the second group of states. The third and fourth groups are each free of states in the first group of states.

In a third aspect, a method is provided for detecting a medical abnormality. A hierarchal model of at least two classifiers is applied to medical data. The first classifier is operable to distinguish between normal and disease states. The second classifier is operable to distinguish between a first diseased state and at least a second diseased state. Which of the normal state, first diseased state and second diseased state is represented by the medical data is identified as a function of the application of the hierarchal model.

In a fourth aspect, a computer readable storage media is provided. Instructions are stored in the storage media for execution by a programmed processor for detecting medical abnormality. Multiple classifiers in a hierarchal model are applied to identify a most appropriate state of at least three or more states for the medical data.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Hierarchal modeling is applied for classification. Rather than one versus all or one versus one schemes to identify a class, multiple stages are applied for distinguishing different groups of classes from each other in a hierarchical approach. Rather than classifying class one versus class two and class one versus class three and class one versus class four, class one is distinguished from the other classes. Assuming class one is not appropriate, class two or another class in the other classes group is then distinguished from the other remaining classes. In a cardiac wall motion example using a five level wall motion scoring, only four classifiers may distinguish between the five states.

The distribution of patient's records among normal cases and diseased cases may be imbalanced. For example, in the ASE scoring scheme, in general the more severe the abnormality, the fewer the number of segments that will have that abnormality. In one distribution of records, it was found that for each level of abnormality, the number of segments found to have that abnormality was reduced by ⅛. That is, in this particular distribution, there were 8 times more normal segments than hypokinetic segments, and 8 times more hypokinetic segments than akinetic segments, etc. Applying hierarchal modeling reduces the extent of distribution imbalance in each of the sub-classifications problems or stages of the hierarchy. The skewed distribution is moderated. Hierarchal modeling may also reduce the risk of misclassifying a majority of cases where a highly accurate classifier is not available. For example, dyskinetic and aneurysmal segments are quite rare. Where learning or training methods are used for classification, an insufficient number of training examples may be available for dyskinesia and aneurysms, resulting in a less distinguishing classifier. Rather than incorporate the less distinguishing classifier into a classification scheme also used for more common cases, the hierarchal model may isolate the classifiers in less common circumstances.

Figure 1:
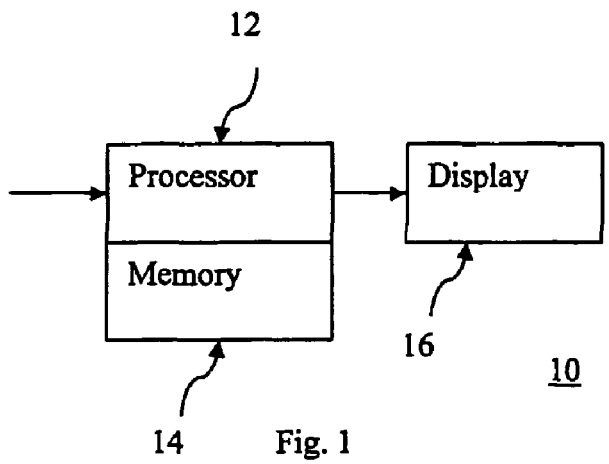
FIG. 1 is a block diagram of one embodiment of a system for applying a hierarchal model.

FIG. 1 shows a system 10 for modeling medical abnormality detection. The system 10 includes a processor 12, a memory 14 and a display 16. Additional, different or fewer components may be provided. The system 10 is a personal computer, workstation, medical diagnostic imaging system, network, or other now known or later developed system for automatically classifying medical information with a processor. For example, the system 10 is a computer aided diagnosis system. Automated assistance is provided to a physician for classifying a state appropriate for given medical information, such as the records of a patient. In one embodiment, assistance is provided for diagnosis of heart diseases or medical conditions, but abnormality diagnosis may be performed for other medical abnormalities, such as associated with the lungs or other organs. The automated assistance is provided after subscription to a third party service, purchase of the system 10, purchase of software or payment of a usage fee.

The processor 12 is a general processor, digital signal processor, application specific integrated circuit, field programmable gate array, analog circuit, digital circuit, combinations thereof or other now known or later developed processor. Any of various processing strategies may be used, such as multi-processing, multi-tasking, parallel processing or the like. The processor 12 is responsive to instructions stored as part of software, hardware, integrated circuits, film-ware, micro-code and the like.

In one embodiment, the processor 12 implements a model or classification system programmed with desired thresholds, filters or other indicators of class. For example, recommendations or other procedures provided by a medical institution, association, society or other group are reduced to a set of computer instructions. In response to patient information automatically determined by a processor or input by a user, the classifier implements the recommended procedure for scoring or identifying normal or abnormal states. In an alternative embodiment, the system 10 is implemented using machine learning techniques, such as training a neural network using sets of training data obtained from a database of patient cases with known diagnosis. The system 10 learns to analyze patient data and output a diagnosis. The learning may be an ongoing process or be used to program a filter or other structure implemented by the processor 12 for later existing cases.

The memory 14 is a computer readable storage media. Computer readable storage media include various types of volatile and non-volatile storage media, including but not limited to random access memory, read-only memory, programmable read-only memory, electrically programmable read-only memory, electrically erasable read-only memory, flash memory, magnetic tape or disk, optical media and the like. In one embodiment, the instructions are stored on a removable media drive for reading by a medical diagnostic imaging system or a workstation networked with imaging systems. An imaging system or work station uploads the instructions. In another embodiment, the instructions are stored in a remote location for transfer through a computer network or over telephone lines to the imaging system or workstation. In yet other embodiments, the instructions are stored within the imaging system on a hard drive, random access memory, cache memory, buffer, removable media or other device.

The memory 14 is operable to store instructions executable by the program processor 12. The instructions are for detecting a medical abnormality or modeling medical abnormality detection. The functions, acts or tasks illustrated in the figures or described herein are performed by the programmed processor 12 executing the instructions stored in the memory 14. The functions, acts or tasks are independent of the particular type of instructions set, storage media, processor or processing strategy and may be performed by software, hardware, integrated circuits, film-ware, micro-code and the like, operating alone or in combination.

Medical data is input to the processor 12 or the memory 14. The medical data is from one or more sources of patient information. For example, one or more medical images are input from ultrasound, MRI, nuclear medicine, x-ray, computer themography, angiography, and/or other now known or later developed imaging modeality. Additionally or alternatively, non-image medical data is input, such as clinical data collected over the course of a patient's treatment, patient history, family history, demographic information, billing code information, symptoms, age, or other indicators of likelihood related to the abnormality detection being performed. For example, whether a patient smokes, is diabetic, is male, has a history of cardiac problems, has high cholesterol, has high HDL, has a high systolic blood pressure or is old may indicate a likelihood of cardiac wall motion abnormality.

The information is input by a user. Alternatively, the information is extracted automatically, such as shown No. 10/287,055 filed on Nov. 4, 2002, entitled "Patient Data Mining") (Ser. No. 10/287,085, filed on Nov. 4, 2002, entitled "Patient Data Mining For Cardiology Screening"), which are incorporated herein by reference. Information is automatically extracted from patient data records, such as both structured and un-structured records. Probability analysis may be performed as part of the extraction for verifying or eliminating any inconsistencies or errors. The system may automatically extract the information to provide missing data in a patient record. The processor 12 performs the extraction of information. Alternatively, other processors perform the extraction and input results, conclusions, probabilities or other data to the processors 12.

The medical data is stored in the memory 14. The memory 14 stores medical data representing one of at least three possible states or classes. In one embodiment, the states are relatively ranked. For example, the five ranked states for cardiac wall motion are used.

The processor 12 implements a classification model for analyzing extracted parameters or other medical data using one or more classifiers. In one exemplary embodiment, the processor 12 classifies a state of cardiac wall motion abnormality based on medical data. The same or different classifiers are implemented in a plurality of stages to score each segment or overall heart wall motion. Wall motion score for each of the various segments of the left ventricle of the heart is performed in accordance with the ASE standard or other standards. Using the recommended views of A4C, A2C, PSAX, PLAX and ALAX, B-mode views are used to obtain quantities, parameters, data or other information associated with each of the segments. Other standards for same or different medical conditions may be used by the processor 12 or model.

The processor 12 is operable to apply different classifiers in a hierarchal model to the medical data. The classifiers are applied sequentially. The first classifier is operable to distinguish between different groups of states. For example, a classifier distinguishes between first and second groups of states. As used herein, a group of states may include a single state. For example, a first group is a normal state and a second group includes a plurality of different disease states. The plurality of disease states includes two or more additional states or other further groupings.

In one embodiment, a state is definitively identified as associated with the medical data. For example, a normal state is identified relative to all diseased states. Since the data is associated with a normal state, the classification pursuant to the hierarchal model ends. Alternatively, classification continues and probabilities are assigned to each of the states. The state with the highest probability is then selected as the state for a given medical record.

After the first classification or stage in the hierarchal model, a second classification or stage is performed. The second classifier is operable to distinguish between remaining groups of states from the original states. The remaining groups of states are a sub-set of the original possible states without any states ruled out or assigned a probability in a previous stage. For example, the remaining states include four diseased states. The second classifier is operable to identify one diseased state from the other three diseased states. The classifier is free of considerations of whether the data is associated with any ruled out or already analyzed states, such as a normal state from preceding stage of the hierarchal model. Given the different purposes or expected states, the classifiers in each of the stages may be different, such as applying different thresholds, using different information, applying different waiting, trained from different datasets, or other differences.

The processor 12 implements additional classifiers to identify a state associated with medical data. For example, two or more different classifiers are provided. Alternatively, two or more classifiers within the hierarchal model are the same, but applied to different datasets. In the myocardial wall example, four different classifiers are applied in four different stages to identify one of five possible states. Alternatively, three classifiers are applied to identify four possible states where one of the possible states includes more than one diseased condition or abnormality.

The display 16 is a CRT, monitor, flat panel, LCD, projector, printer or other now known or later developed display device for outputting determined information. For example, the processor 12 causes the display 16 at a local or remote location to output data indicating a state associated with a given medical record, probability associated with the one or more states, or other process related information. The output may be stored with or separate from the medical data.

Figure 2:
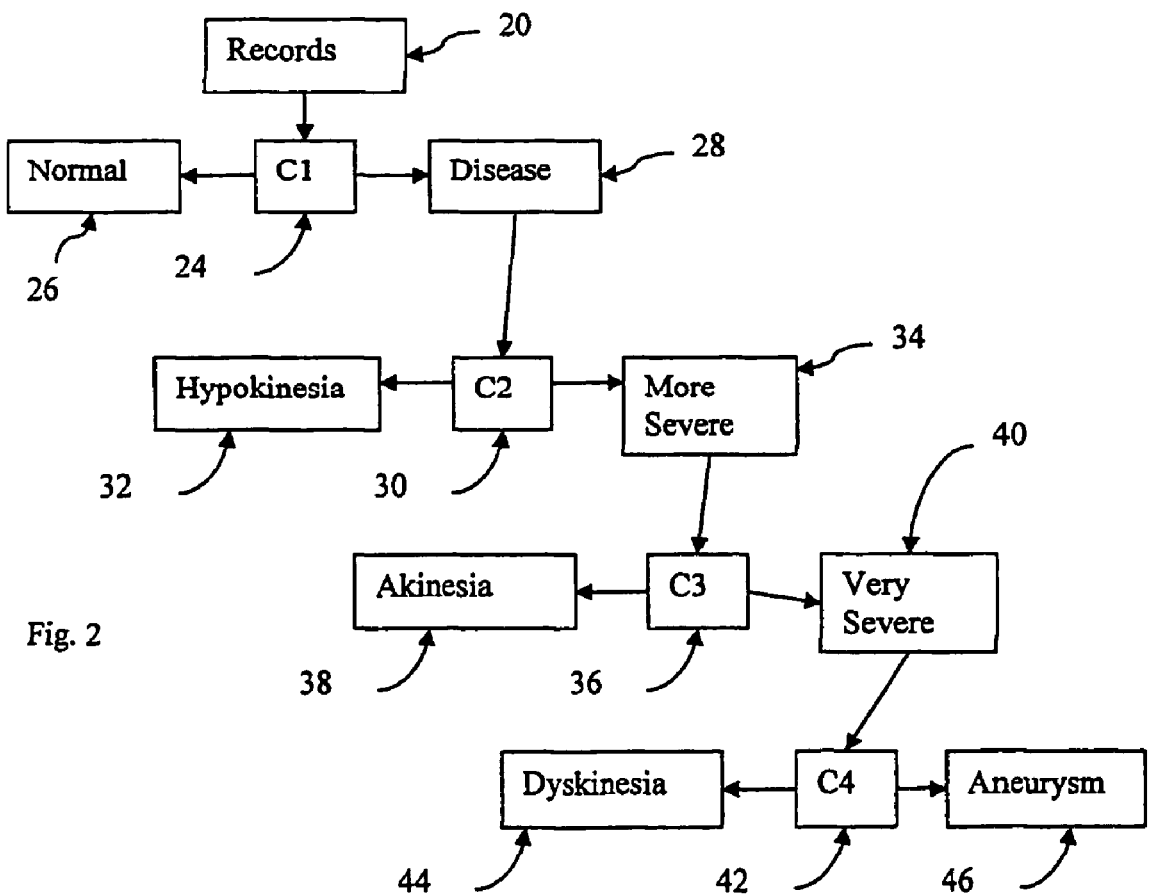
FIG. 2 is a flow chart diagram showing one embodiment of a hierarchal model process.

FIG. 2 shows one embodiment of a method for detecting a medical abnormality. The method represents modeling medical abnormality detection. The method is implemented using the system 10 of FIG. 1 or a different system. Additional, different or fewer acts than shown in FIG. 2 may be provided in the same or different order. For example, acts 24, 30, 36 and/or 42 may not be performed in response to user input or automatically.

The flow chart shown in FIG. 2 is for applying a hierarchal model to medical data for identifying cardiac wall motion scores or abnormality. The same of different hierarchal model may be used for detecting other abnormalities, such as other cardiac abnormalities or abnormalities associated with other organs or tissue.

In Act 20, medical data representing one of at least three possible states is obtained. For example, the medical data is obtained automatically, through user input or a combination thereof for a particular patient or group of patients. In the example of FIG. 2, the medical data is for a patient being analyzed with respect to cardiac wall motion. Using the ASE standard, the medical data is associated with one of five different states—normal, hypokinesia, akinesia, dyskinesia and aneurysm. In alternative embodiments, a disease state is assumed and a normal state is not provided. A greater or fewer number of disease states may be provided.

In Act 22, a hierarchal model with at least two classifiers is applied to the medical data obtained in Act 20. The hierarchal model distinguishes between various states associated with the medical data. For example, the hierarchal model distinguishes between normal, hypokinesia and akinesia states. Different or the same classifiers are sequentially applied to the data in the hierarchal model. For example as shown in FIG. 2, four different classifiers are applied in sequential order. The later occurring applications of classifiers are only performed when the previous applications did not identify one or more states with a desired probability. If a prior classifier indicates a singular or multiple states with sufficient accuracy, the process may end or may branch. The subsequent classifications on the branch of the hierarchal model not appropriate for a given medical record are not applied. Alternatively, all or a set number of classifiers are applied for determining relative probabilities. By applying the hierarchal model in Act 22, a state represented by the medical data is identified.

In Act 24, a first stage of classification is performed. A processor automatically classifies medical data between one group of states and another group of states. For example and as shown in FIG. 2, the classifying of Act 24 classifies between a normal state shown at 26 and four possible disease states shown at 28. The disease states represent all possible disease states but may alternatively represent fewer than all possible disease states. For example, the disease states represent hypokinesia, akinesia, dyskinesia and aneurysm states. As another example, the classification is between a group of two or more states and another group of two or more states.

Where the classifying of Act 24 indicates a single or conclusory state, such as the normal state 26, the process may cease or end. Alternatively, the classifying of Act 24 rules out one or more states, such as the normal state 26. The classifying indicates the medical data is associated with one or more of the disease states shown at 28.

The classification is performed with neural network, filter, algorithm, or other now-known or later developed classifier or classification technique. The classifier is configured or trained for distinguishing between the desired groups of states. The inputs to the classifier include one, more, a subset or all parameters suggested by a medical standard or other selected parameters for distinguishing between different groups of states. For example, the classification disclosed in (application Ser. No. 10/876,803), the disclosure of which is incorporated herein by reference, is used. The inputs are received directly from a user, determined automatically, or determined by a processor in response to or with assistance from user input.

For automatic determination, data mining may be used for determining clinical information, such as the age or other medical information for a particular patient. Image analysis may be performed with a processor or automatically for identifying other characteristics associated with the medical data. For example, ultrasound images are analyzed to determine wall motion, wall thickening, wall timing and/or volume change associated with a heart or myocardial wall of the heart. Additional, different or fewer parameters derived from image information may be used. The process is performed separately for each segment.

Any portion of the heart may be tracked for motion data. For example, the inner heart wall is tracked to determine an amount of contraction, amount of expansion, a difference between maximum and minimum contraction, a difference in the amount of motion between different portions of the heart, a velocity, a timing of the motion, an acceleration or other characteristic of motion of the heart. A global shape or local motion, such as an endocardial wall or epacardial wall, is tracked. The motion is tracked by identifying one or more regions of interest, such as in response to user input or automatic border detection. The same or similar region is identified in a series of images using the minimum sum of absolute differences, correlation, Doppler based velocity information or other techniques for determining motion parameters of an identified region. In one embodiment, the methods described (Ser. No. 10/794,476, filed on Mar. 5, 2003), the disclosure of which is incorporated herein by reference, are used. One or more motion tracking parameters are calculated and output for use in classification to characterize a state associated with the patient data.

To determine one or more thickening parameters, the inner and outer borders of the myocardial wall or other portion of the heart are determined. The contours are determined over a time frame, such as during the systole phase, to indicate an amount of wall thickening over the time frame. The thickness is determined at a user indicated region, an automatically detected region or at a plurality of regions. An average or separate parameters may be calculated for each of the plurality of regions. Using the known scan pattern, the distance between the inner and outer wall at the desired regions is determined. Inner and outer boundaries are determined in response to user input or automatically. For automatic determination, automatic border detection may be provided. For example, a gradient associated with a sequence of images is determined to indicate outer and inner wall boundaries through the sequence. Other methods may be used, such as described (application Ser. No. 10/794,476), (application Ser. No. 10/991,933, filed on Oct. 1, 2004), (application Ser. No. 10/957,380, filed on Nov. 18, 2004), the disclosures of which are incorporated herein by reference.

Using the same or different border detection techniques, a volume, a volume change, volume flow, volume ejection fraction or other volume characteristic associated with the heart is determined. For example, the left ventricle volume change between systole and diastole phases is determined. The inner contour of the myocardial wall or other heart boundary is tracked. An area associated with the boundary in a particular view is determined. Where the boundary has gaps, the gaps are filled by curve fitting or a linear connection between closest end points. The area is then converted to a volume using any now known or later developed approximations. Where three-dimensional imaging data is available, the volume may be calculated without approximation or extrapolation.

One or more timing parameters indicate relative motion of different portions of the heart, such as indicating relative motion of the septum and the lateral wall. The difference in onset of motion relative to the heart cycle of two or more locations of the heart indicates a level of asynchrony or dysynchrony. Difference is in total time of motion, onset of motion, completion of motion or other timing events may be used. In one embodiment, the asynchrony calculations or phase information disclosed (application Ser. No. 11/051,224 filed on Feb. 4, 2005 and entitled CARDIAC WALL MOTION ASYCHRONY ANALYSIS IN APICAL FOUR-CHAMBER VIEW WITH ECHO PHASE IMAGING) Provisional Ser. No. 60/542,121), or (application Ser. No. 10/713,453, filed on Nov. 14, 2003), the disclosures of which are incorporated herein by reference, are used. For example, a sequence of images is analyzed to determine the onset time of periodical motion. Pixel intensity changes in two or three dimensional image sequences are analyzed with a Fourier transform. The relative phases of the first or fundamental harmonic to the heart cycle identifies the onset time of motion for different regions.

In Act 30, medical data is classified between the remaining groups of states. A processor applies a classifier to the medical data, such as the same medical data obtained in Act 20 and used in Act 24 or different medical data. In the example shown in FIG. 2, the classifying of Act 30 distinguishes between groups of disease states, such as distinguishing between hypokinesia at 32 and the remaining disease states of akinesia, dyskinesia and aneurysm at 34. The classifier applied in Act 30 is the same or different than the classifier applied in Act 24. The classification is performed in response to the same or different input parameters. Since one or more states have been ruled out, the classifying of Act 30 in one embodiment uses parameters and a classifier selected for distinguishing between the desired disease states without distinguishing any ruled out states. The classification is more focused on and more likely to accurately distinguish between the different remaining states.

In Act 36, the medical data is classified between the remaining medical states. For example and as shown in FIG. 2, the classifier applied in Act 36 identifies a single state of akinesia at 38 from to other possible states of dyskinesia and aneurism at 40. Classification is performed using the same or different classifier and/or input parameters than used in Acts 24 or 30. In Act 42, the processor classifies the medical data between the two remaining states of dyskinesia at 44 and aneurysm at 46. Each classification is focused on classifying between remaining states or different groups of remaining states. Different parameters, inputs, data, algorithms, classifiers, or other characteristics are applied since one or more other states have been ruled out.

In the hierarchal structure shown in FIG. 2, four classifiers or separate classifications are performed to distinguish between five possible states. Since each of the states is associated with a ranked order, such as from normal to the most severe, a linear tree structure is provided.

Figure 3:
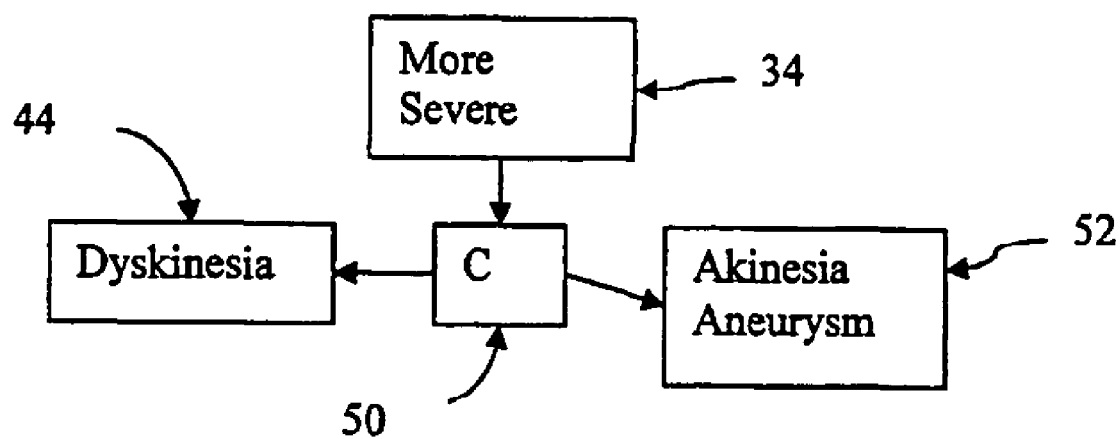
FIG. 3 is another embodiment of one stage of a hierarchal model for classification.

FIG. 3 shows an alternative embodiment of Act 50 for the classification shown in Act 36. In Act 50, the remaining possible three states from Act 34 are classified. In particular, a processor classifies medical data to distinguish a mid level state of three ranked states from the less and more severe states. For example, the dyskinesia state at 44 is classified or distinguished from akinesia and aneurism states at 52. Subsequent classification may then be used to distinguish between the akinesia and aneurism states at 52. Other changes in the order of classification may be performed within the structure shown in FIG. 2. The order of the classifications may be altered, such as distinguishing between (a) one or more disease states and (b) a normal and other disease states. Other combinations of groups of states may be distinguished from other groups of states, such as distinguishing normal and hypokinesia from more severe states or distinguishing hypokinesia and dyskinesia from normal, akinesia and aneurism states. Additional branches in the model distinguish between the remaining states based on a distinction or classification in a previous stage.

Processor implementation of the hierarchal model may fully distinguish between all different possible states or may be truncated or end depending on the desired application. For example, medical practitioners may be only interested in whether the state associated with the patient record is normal, minor diseased or more severely diseased, such as distinguishing between the normal, hypokinesia and more severe situations. The process may then terminate. The learning processes or other techniques for developing the classifiers may be based on the desired classes or states rather than the standard model states.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for modeling in medical abnormality detection, the method comprising:

obtaining medical data representing characteristics of a patient and corresponding to one of at least five possible ranked states, the at least five possible ranked states being a first, a second, fourth and fifth state;

hierarchically classifying with a processor the medical data between the first state and a group of at least the second, third, fourth and fifth states;

hierarchically classifying with the processor the medical data between the second state and a group of at least the third, fourth and fifth states;

hierarchically classifying with the processor the medical data between the third state and a group of at least the fourth and fifth states;

hierarchically classifying with the processor the medical data between the fourth state and at least the fifth state; and displaying an output indicating an actual state, determined from the classifying acts, of the patient.

2. The method of claim 1 wherein the at least five possible ranked states comprise five cardiac wall motion states, the first state being a normal state.

3. The method of claim 2 wherein classifying between the first state and the group of at least the second, third, fourth and fifth state comprises classifying between the normal state and all disease states, the disease states including the second and third states of the five cardiac wall motion states, and wherein classifying between the second and a group of at least the third, fourth and fifth states comprises classifying between one or more of the disease states and one or more different ones of the disease states, the disease states comprising hypokinesia, akinesia, dyskinesia, and aneurysm.

4. The method of claim 2 wherein classifying between the first state and the group of at least the second, third, fourth and fifth states comprises classifying between the normal state and all disease states, the disease states including the second and third states of the five cardiac wall motion states, and wherein classifying between the second state and a group of at least the third, fourth and fifth states comprises classifying between the second state and three other disease states;

further comprising:

classifying between the third state and two other disease states; and classifying between the fourth state and the fifth state.

5. The method of claim 1 wherein classifying between the first state and the group of at least the second, third, fourth and fifth states is performed before classifying between the second state and a group of at least the third, fourth and fifth states, classifying between the first state and the group of at least the second, third, fourth and fifth states being operable to rule out the first state from possible states.

6. The method of claim 1 wherein classifying between the first state and the group of at least the second, third, fourth and fifth states comprises classifying between (a) another group comprising the first state and a fourth state and (b) the group of at least the second, third, fourth and fifth states.

7. The method of claim 1 wherein a number of classifying acts is one less than a total number of possible ranked states.

8. The method of claim 1 wherein classifying between the first state and the group of at least the second, third, fourth and fifth states is performed as a function of a different process or parameter than classifying between the second state and a group of at least the third, fourth and fifth states.

9. A system for modeling in medical abnormality detection, the method comprising:

a memory operable to store medical data representing one of at least three possible ranked states;

a processor operable to apply to the medical data a first classifier in a hierarchal model, the first classifier operable to distinguish between first and second groups of states of the at least three possible ranked states, and the processor operable to apply to the medical data a second classifier in the hierarchal model, the second classifier operable to distinguish between third and fourth groups of states of the at least three possible states, the third and fourth groups being sub-sets of the second group of states and each being free of states of the first group of states; and a display for displaying an output indicating an actual state, determined from the classifiers, of the patient.

10. The system of claim 9 wherein the at least three possible ranked states comprise cardiac wall motion states.

11. The system of claim 9 wherein the first group comprises a normal state, the second group comprises at least first and second disease states, the third group comprises at least the first disease state and the fourth group comprises at least the second disease state.

12. The system of claim 9 wherein the processor is operable to apply the first classifier before the second classifier and operable to apply at least a third classifier in the hierarchal model after the second classifier.

13. The system of claim 9 wherein the first group consists of a first state and the second group comprises the third and fourth groups.

14. The system of claim 9 wherein the first classifier is different than the second classifier.

15. A method for detecting a medical abnormality, the method comprising:

applying with a processor a hierarchal model of at least four classifiers to medical data representing a patient, the first classifier operable to distinguish between a normal state and disease states, the second classifier operable to distinguish between a first disease state and at least a second disease state, the third classifier operable to distinguish between the second disease state and at least a third disease state, the fourth classifier operable to distinguish between the third disease state and at least a fourth disease state;

identifying which of the normal state, first disease state, second disease state, third disease state, and fourth disease state is represented by the medical data as a function of the applying; and outputting the identified slate of the patient.

16. The method of claim 15 wherein applying comprises distinguishing between the normal state, the first disease state comprising a hypokinesia state, and the second disease state comprising an akinesia state, the distinguishing being performed with sequential application of the first and second classifiers.

17. The method of claim 15 wherein the first classifier is operable to distinguish between (a) the normal state and (b) all disease states, the disease states including hypokinesia, akinesia, dyskinesia, and aneurysm states, the second classifier operable to distinguish between (a) the hypokinesia state and (b) akinesia, dyskinesia, and aneurysm states; wherein the third classifier is operable to distinguish between (a) the akinesia state and (b) dyskinesia mad aneurysm states, and the fourth classifier is operable to distinguish between (a) the dyskinesia state and (b) the aneurysm state; and wherein the first, second, third and fourth classifiers are applied in sequential order, the later occurring applications only being performed where the previous applications indicated (b) states.

18. The method of claim 15 wherein applying the hierarchal model comprises applying the first classifier prior to the second classifier, and applying the second classifier only if the first classifier indicates the medical data to not represent a normal state.

19. In a computer readable storage media having stored therein data representing instructions executable by a programmed processor for detecting medical abnormality, the storage media comprising instructions for:

applying a hierarchal model of at least four classifiers to medical data, the first classifier operable to distinguish between a normal state and disease states, the second classifier operable to distinguish between a first disease state and at least a second disease state, the third classifier operable to distinguish between the second disease state and at least a third disease state, the fourth classifier operable to distinguish between the third disease state and at least a fourth disease state; and identifying which of the normal state, first disease state, second disease state, third disease state, and fourth disease state is represented by the medical data as a function of the applying.

20. The instructions of claim 19 wherein applying comprises distinguishing between the normal state, the first disease state comprising a hypokinesia state, and the second disease state comprising a akinesia state, the distinguishing being performed with sequential application of the first and second classifiers.

21. The instructions of claim 19 wherein the first classifier is operable to distinguish between (a) the normal state and (b) all disease states, the disease states including hypokinesia, akinesia, dyskinesia, and aneurysm states, the second classifier operable to distinguish between (a) the hypokinesia state and (b) akinesia, dyskinesia, and aneurysm states;

wherein the third classifier is operable to distinguish between (a) the akinesia state and (b) dyskinesia and aneurysm states, and the fourth classifier is operable to distinguish between (a) the dyskinesia state and (b) the aneurysm state; and wherein the first, second, third and fourth classifiers are applied in sequential order, the later occurring applications only being performed where the previous applications indicated (b) states.

22. The instructions of claim 19 wherein applying the hierarchal model comprises applying the first classifier prior to the second classifier, and applying the second classifier only if the first classifier indicates the medical data to not represent a normal state.

* * * * *